US005741479A

United States Patent [19]
Masterman et al.

[11] Patent Number: 5,741,479
[45] Date of Patent: Apr. 21, 1998

[54] DESENSITIZING TEETH WITH DEGRADABLE PARTICLES

[75] Inventors: Thomas Craig Masterman; Jean L. Spencer, both of Boston, Mass.

[73] Assignee: Gillette Canada Inc., Kirkland, Canada

[21] Appl. No.: 471,419

[22] Filed: Jun. 6, 1995

Related U.S. Application Data

[62] Division of Ser. No. 336,486, Nov. 9, 1994.

[51] Int. Cl.$^6$ .............................. A61K 7/16; A61K 9/14; A61C 5/00; C09K 3/12
[52] U.S. Cl. ........................ 424/49; 424/401; 424/422; 424/426; 424/435; 424/489; 424/498; 424/501; 424/502; 433/215; 433/217.1; 433/228.1; 106/35
[58] Field of Search .......................... 424/49, 401, 422, 424/426, 435, 489, 498, 501, 502; 433/215, 217.1, 228.1; 106/35

[56] References Cited

U.S. PATENT DOCUMENTS

| | | |
|---|---|---|
| Re. 21,197 | 9/1939 | Hill et al. |
| Re. 24,899 | 11/1960 | Green |
| 1,921,722 | 8/1933 | Berendes et al. |
| 1,928,346 | 9/1933 | Axelrod |
| 1,984,733 | 12/1934 | Forbing |
| 2,304,478 | 12/1942 | Rosenzweig |
| 2,558,992 | 7/1951 | Stott |
| 2,914,443 | 11/1959 | Lynch |
| 2,994,642 | 8/1961 | Bossard |
| 3,122,483 | 2/1964 | Rosenthal |
| 3,226,297 | 12/1965 | Thuresson et al. |
| 3,258,805 | 7/1966 | Rossnan |
| 3,357,950 | 12/1967 | La Follette |
| 3,357,951 | 12/1967 | Adams, Jr. |
| 3,380,848 | 4/1968 | Horowitz |
| 3,450,813 | 6/1969 | Muhler |
| 3,475,369 | 10/1969 | Blunt |
| 3,523,906 | 8/1970 | Vrancken |
| 3,542,519 | 11/1970 | Montalto et al. |
| 3,689,636 | 9/1972 | Svajda |

(List continued on next page.)

FOREIGN PATENT DOCUMENTS

| | | |
|---|---|---|
| 0 079 400 | 5/1983 | European Pat. Off. |
| 0 244 118 | 11/1987 | European Pat. Off. |
| 0 441 317 | 8/1991 | European Pat. Off. |
| 0 480 785 | 4/1992 | European Pat. Off. |
| 39 23002 | 1/1991 | Germany |
| 62-175410 | 8/1987 | Japan |
| 62-175412 | 8/1987 | Japan |
| WO 90/10400 | 3/1990 | WIPO |
| WO 93/05680 | 1/1993 | WIPO |
| WO 94/08562 | 4/1994 | WIPO |

OTHER PUBLICATIONS

Juliano, "Controlled delivery of drugs: an overview and prospectus", *Drug Delivery Systems* (1980).

Ratner, "Biomedical Applications of Synthetic Polymers", *Comprehensive Polymer Science*, vol. 7 (1989).

Mathiowitz et al., "Morphology of Polyanhydrine Microsphere Delivery Systems", *Scanning Microscopy*, 4:329–340 (1990).

Pekarek et al., "Double–walled polymer microspheres for controlled drug release", *Letters to Nature*, 367:258–260 (Jan. 1994).

Gref et al., "Biodegradable Long–Circulating Polymeric Nanospheres", *Science*, 263:1600–1603 (Mar., 1994).

Müller et al., "In vitro characterization of poly(methyl–methacrylate) nanoparticles and correlation to their vivo fate", *Journal of Controlled Release*, 20:237–246 (1992).

Gennaro, "Sedatives and Hypnotics", *Remington's Pharmaceutical Sciences*, 18th ed. (Mack Publishing Co. 1990), pp. 1063–1064.

Brännström, "The Dentinal Tubules and the Odontoblast Processes", *Acta Odontol Scand*, 30:291–311 (1972).

Garriott et al., "Death in the Dental Chair: Three Drug Fatalities in Dental Patients", *J. Toxicol. Clin. Toxicol.*, 19:987–995 (1982–1983).

Porter, "Barbiturate and Non–Barbiturate Premedication Before Nitrous Oxide an Aesthesia for Children, *Brit. Dental J.*, 125:546–548 (1968).

Rye et al., "Clinical Notes in Therapeutics", *J. Oral Med.*, 41:66–67 (1986).

Zoryan et al., *Stromatologiia*, 3:71–74 (1975) (English Abstract Included).

Berman, "Dentinal Sensation and Hypersensitivity", 56:216–222, *J. Periodontal* (1984).

Brännström et al., "A Study on the Mechanism of Pain Elicited from the Dentin", *J. Dental Res.*, 43:619–625 (1964).

Gunji, "Morphological Research on the Sensitivity of Dentin", *Arch. Histo. J.*, 45:45–67 (1982).

Lecointre et al., "Controlled Trial of the Action of a Toothpaste Containing Nicomethanol Hydrofluoride . . . ", *J. Int. Med. Res.*, 14:217–222 (1986).

Närhi et al., "Response of intradental nerve fibres to stimulation of dentine and pulp", *Acte. Physiol. Scand.*, 115:173–178 (1982).

Pashley et al., "Pain produced by topical anesthetic ointment", *Endodont. Dent. Traumatol*, 3:80–82 (1987).

Pleasants et al., "Dialog in treatment of dental pain", *Oral Surg., Oral Med. & Oral Pathol.*, 28:163–165 (1969).

Trowbridge, "Intradental Sensory Units: Physiological and Clinical Aspects", *J. of Endodontics*, 11:489–498 (1985).

Yoshiyama et al., "Transmission Electron Microscopic Characterization of Hypersensitive Human Radicular Dentin", *J. Dent. Res.*, 69(6):1293–1297 (1990).

Pashley et al., "Dentin permeability: Effects of cavity varnishes and bases", *J. Prosthet. Dent.*, 53(4):511–516 (1985).

*Primary Examiner*—Shep K. Rose
*Attorney, Agent, or Firm*—Fish & Richardson P.C.

[57] ABSTRACT

A method for desensitizing a hypersensitive tooth in a patient includes contacting exposed tubules with particles including a degradable material.

9 Claims, 2 Drawing Sheets

U.S. PATENT DOCUMENTS

| | | | |
|---|---|---|---|
| 3,699,979 | 10/1972 | Muhler et al. | |
| 3,772,431 | 11/1973 | Mlkvy et al. | |
| 3,773,919 | 11/1973 | Boswell et al. | 424/19 |
| 3,810,479 | 5/1974 | Miles . | |
| 3,839,568 | 10/1974 | Samour et al. | |
| 3,863,006 | 1/1975 | Hodosh . | |
| 3,868,447 | 2/1975 | Kliment . | |
| 3,887,699 | 6/1975 | Yolles | 424/19 |
| 3,888,976 | 6/1975 | Mlkvy et al. | |
| 3,919,409 | 11/1975 | Perla et al. | |
| 3,920,837 | 11/1975 | Schmidt-Dunker et al. | |
| 3,934,001 | 1/1976 | Watson . | |
| 3,937,830 | 2/1976 | Samour . | |
| 3,943,949 | 3/1976 | Ashton et al. | |
| 3,956,480 | 5/1976 | Dichter et al. | |
| 3,957,964 | 5/1976 | Grimm, III . | |
| 3,957,968 | 5/1976 | Cordon . | |
| 3,959,457 | 5/1976 | Speaker et al. | |
| 3,978,206 | 8/1976 | Naumann et al. | |
| 3,991,766 | 11/1976 | Schmitt et al. | 128/335.3 |
| 3,992,336 | 11/1976 | Faucher et al. | |
| 4,007,259 | 2/1977 | Patino et al. | |
| 4,011,309 | 3/1977 | Lutz . | |
| 4,018,729 | 4/1977 | Faucher et al. | |
| 4,033,365 | 7/1977 | Klepak et al. | |
| 4,057,621 | 11/1977 | Pashley et al. | |
| 4,102,992 | 7/1978 | Davis . | |
| 4,134,969 | 1/1979 | Schmidt-Dunker . | |
| 4,138,383 | 2/1979 | Rembaum et al. | |
| 4,155,870 | 5/1979 | Jorgensen . | |
| 4,324,630 | 4/1982 | Sugita et al. | |
| 4,339,429 | 7/1982 | Raaf et al. | |
| 4,348,378 | 9/1982 | Kosti . | |
| 4,389,393 | 6/1983 | Schor et al. | |
| 4,534,839 | 8/1985 | Schaefer . | |
| 4,619,701 | 10/1986 | Angrick et al. | |
| 4,631,185 | 12/1986 | Kim . | |
| 4,634,589 | 1/1987 | Scheller . | |
| 4,668,295 | 5/1987 | Bajpaj | 106/85 |
| 4,678,814 | 7/1987 | Rembaum . | |
| 4,685,883 | 8/1987 | Jernberg . | |
| 4,710,372 | 12/1987 | Scheller . | |
| 4,751,072 | 6/1988 | Kim . | |
| 4,762,373 | 8/1988 | Amos et al. | |
| 4,780,320 | 10/1988 | Baker | 424/493 |
| 4,802,255 | 2/1989 | Breuer et al. | |
| 4,818,542 | 4/1989 | Deluca et al. | 424/491 |
| 4,828,955 | 5/1989 | Kasai et al. | |
| 4,837,007 | 6/1989 | Duckworth et al. | |
| 4,861,627 | 8/1989 | Mathiowitz et al. | |
| 4,867,988 | 9/1989 | Chernack . | |
| 4,873,269 | 10/1989 | Nakazato . | |
| 4,889,850 | 12/1989 | Thornfeldt et al. | |
| 4,892,736 | 1/1990 | Goodson . | |
| 4,904,479 | 2/1990 | Illum . | |
| 4,911,922 | 3/1990 | Masuhara et al. | |
| 4,917,892 | 4/1990 | Speaker et al. | |
| 4,919,939 | 4/1990 | Baker | 424/493 |
| 4,959,220 | 9/1990 | Yamamoto et al. | |
| 4,963,347 | 10/1990 | Humphries et al. | |
| 4,978,391 | 12/1990 | Jones . | |
| 4,980,150 | 12/1990 | Keith . | |
| 4,986,288 | 1/1991 | Kent et al. | |
| 4,990,327 | 2/1991 | Neirinckx . | |
| 4,992,258 | 2/1991 | Mason . | |
| 5,000,941 | 3/1991 | Chernack . | |
| 5,037,818 | 8/1991 | Sime . | |
| 5,061,106 | 10/1991 | Kent . | |
| 5,077,049 | 12/1991 | Dunn et al. | 424/426 |
| 5,082,653 | 1/1992 | Pan et al. | |
| 5,085,850 | 2/1992 | Pan et al. | |
| 5,098,711 | 3/1992 | Hill et al. | |
| 5,130,412 | 7/1992 | Wellinghoff et al. | |
| 5,141,290 | 8/1992 | Mairon . | |
| 5,143,662 | 9/1992 | Chesterfield et al. | 264/8 |
| 5,147,632 | 9/1992 | Pan et al. | |
| 5,185,155 | 2/1993 | Behan et al. | |
| 5,211,939 | 5/1993 | Turesky et al. | |
| 5,250,288 | 10/1993 | Turesky et al. | |
| 5,252,577 | 10/1993 | Breuer et al. | |
| 5,324,519 | 6/1994 | Dunn et al. | 424/426 |
| 5,366,733 | 11/1994 | Brizzolara et al. | 424/426 |
| 5,368,859 | 11/1994 | Dunn et al. | 424/426 |
| 5,424,346 | 6/1995 | Sinclair | 524/108 |

DESENSITIZING TEETH WITH DEGRADABLE PARTICLES

This is a divisional of copending application Ser. No. 08/336,486, on Nov. 9, 1994 by Thomas C. Masterman and Jean L. spencer for DESENSITIZING TEETH WITH DEGRADABLE PARTICLES.

BACKGROUND OF THE INVENTION

The invention relates to desensitizing teeth.

The dentin layer in a tooth generally contains channels, or tubules, extending from the pulpal surface to the peripheral surface located underneath the enamel and cementum. Loss of enamel and/or gingival recession accompanied by loss of cementum may expose these tubules in the dentin. It has been theorized that these exposed tubules are responsible, in part, for hypersensitivity to mechanical pressure or hot or cold fluids.

The problem of hypersensitive teeth is well-recognized, and various treatments have been proposed in the art. Pashley et al., U.S. Pat. No. 4,057,021, describes desensitizing hypersensitive teeth by applying an aqueous solution of alkali metal salts and ammonium oxalate to the surface of the teeth. Kim, U.S. Pat. Nos. 4,631,185 and 4,751,072 describes desensitizing teeth by treatment with potassium salts. Neirinckx, U.S. Pat. No. 4,990,327, describes desensitizing teeth with strontium ion and fluoride ion. Mason, U.S. Pat. No. 4,992,258, describes desensitizing teeth by applying a dentifrice including a montmorillonite clay. Lutz, U.S. Pat. No. 4,011,309, describes a desensitizing dentifrice composition that includes citric acid, sodium citrate, and non-ionic polyol surfactant. Mlkvy et al., U.S. Pat. Nos. 3,888,976 and 3,772,431 describe using a zinc or strontium ion containing astringent-desensitizing agent in an effervescent mouthwash tablet. Hodosh, U.S. Pat. No. 3,863,006, describes desensitizing teeth with a nitrate salt. Svajda, U.S. Pat. No. 3,689,636, describes desensitizing teeth with solutions of chloride salts. Rosenthal, U.S. Pat. No. 3,122,483, describes desensitizing teeth with strontium ions. Scheller, U.S. Pat. Nos. 4,634,589 and 4,710,372, describe a dentifrice containing apatite particles for treating hypersensitive teeth. Turesky et al., U.S. Pat. No. 5,250,288, describes desensitizing a hypersensitive tooth by treating the surface of the tooth with charged polymeric particles.

SUMMARY OF THE INVENTION

The invention features a method for desensitizing a hypersensitive tooth in a patient. The method includes contacting the tubules exposed on the surface of a hypersensitive tooth with particles that contain a degradable material. The particles block or cover the tubules in the dentin layer, which results in desensitization. Importantly, particularly when the particles are composed substantially only of the degradable material, for the most part nothing remains of the particles in the mouth or body once the degradable material degrades.

The preferred particles have an average size of between 0.01 micron and 3 microns, more preferably between 0.2 micron and 0.6 micron. The particles may be microspheres, and may have a charged outer surface that help the particles cling to the surface of the tooth and block the exposed tubules. The preferred particles optionally may include an antimicrobial agent absorbed on the surface, as described in U.S. Pat. No. 5,300,290, or dispersed throughout the particles, as described in U.S. Ser. No. 08/322,926, filed Oct. 13, 1994, which is assigned to the same assignee as the present application. The preferred particles also optionally may include an analgesic compound (e.g., benzocaine, barbital), which can be absorbed on the outer surface of the particle as described in U.S. Pat. No. 5,252,577, or dispersed throughout the article. These patents and patent application are incorporated by reference herein.

In a preferred method, the surface of the hypersensitive tooth is polished, and a dispersion of the particles is applied to the polished surface for at least one minute. A preferred method of applying the particles is by brushing the teeth with a toothbrush having bristles that include the particles.

Some preferred particles are stable when stored, e.g., as an aqueous dispersion, because the preferred particles have non-porous water-stable exteriors composed of a water-stable material. Some preferred water-stable materials are disrupted by mechanical stresses, such as chewing, flossing, and brushing. Such water-stable materials include hydrophobic materials like poly(methyl methacrylate), polystyrene, beeswax, carnauba wax, petroleum wax, and similar materials which do not significantly degrade when exposed to oral enzymes. Other preferred water-stable materials degrade when exposed to oral enzymes. Such materials include polyhydroxyalkanoic acids, glycolipids, glycerides, and phospholipids.

In some preferred embodiments, the water-stable material functions as both a degradable material and a water-stable exterior coating. A particularly preferred material for this embodiment is glycerol distearate.

Preferred degradable polymers include polyglycolic acid, polylactic acid, and copolymers of glycolic acid and lactic acid, and esters of glycerol like glycerol distearate.

"Degradable material", as used herein, means a material which degrades within three months when placed in the mouth of a typical patient. The materials degrade as a result of exposure to one or more enzymes that commonly are found in the mouth. These enzymes include lipases, proteases, and glucosidases. Specific enzymes include parotid amylase, hyaluronidase, beta-glucoronidace, chondroitin sulfatase, amino acid decarboxylases, catalase, peroxidase (such as lacto peroxidase), collagenase, and lysozyme.

"Water-stable exterior", as used herein, means that the exterior surface of the particle is composed of a material that does not chemically degrade or swell when exposed to water. For example, as a result of the water-stable exterior, if the particle includes an anti-microbial agent or an analgesic, substantially no (i.e., less than 5% by weight) anti-microbial agent or analgesic leaches from the particle when the particle is placed in distilled water (at a concentration of 10% of the dispersion by weight) at room temperature for a month.

The invention provides an effective, straightforward way to desensitize teeth. Without being bound to any theory, it is believed that the invention is effective at least in part because the particles block the tubules in the teeth, making it more difficult for external stimuli like hot or cold temperatures to affect the nerve in the pulp. When some of the particles blocking the tubules eventually wash out of the tubules or degrade, they are easily replenished by an additional application of particles.

Other features and advantages of the invention will be apparent from the description of the preferred embodiment thereof, and from the claims.

DESCRIPTION OF THE PREFERRED EMBODIMENTS

Figure 1A:
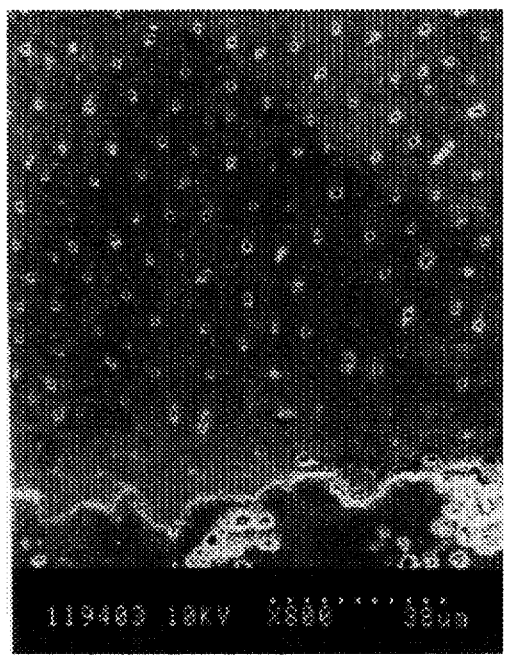
FIGS. 1a and 1b are electron micrographs of a dentin surface prior to exposure to the particles of the invention.

The more preferred particles have an average diameter of less than 0.6 micron. Larger particles may not fit as well in dentin tubules, and as a result may not be as effective at blocking the tubules and desensitizing the teeth.

The particles include a degradable material. Preferred degradable materials include polycaprolactone, polydecalactone, poly(sebacic anhydride), sebacic acid-co-1,3-bis(carboxy-phenoxypropane), sebacic acid-co-1,6-bis(carboxyphenoxy-hexane), dedecanoic-co-1,3-bis(carboxyphenoxypropane), dedecanoic-co-1,6-bis(carboxyphenoxyhexane), albumin and derivatives, gelatin and derivatives, starch and derivatives, gum arabic, cellulose and derivatives, polysorbate and derivatives, agarose, lectins, galactose, functionalized nylons (e.g. benzylated), proteins (synthetic and natural), polyorthoesters, polyorthoformate, polyureas, polyurethanes, poly(amide-enamine)s, polyvinylalcohol, polyenolketone (PEK), polyHema, functionalized polyHema, ethylenevinylacetate copolymers, functionalized polymers and copolymers of lactic and glycolic acid, lactic acid homopolymer, glycolic acid copolymer, copolymers of lactic acid and glycolic acid, polyhydroxybutyrate, poly(esterimides), functionalized silicones, poly(anhydrides), poly(malic acid), and polyhydroxyalkanoic acids from synthetic or natural sources (e.g., bacterial, fungi and the like).

Other preferred degradable materials include monomeric species and mixed monomeric/polymeric species such as liposomes, glycolipids, fatty acids, glycerides, carnauba wax, and phospholipids. The degradable materials can be included in organic/inorganic composites (covalent or mixed) by combining any of the polymers listed above with minerals such as silica, alumina, kaolin, morierite, cordierite, zirconia minerals and the like; any of the monomeric and monomer/polymer species listed above mixed or covalently bound with minerals such as silica, alumina, kaolin, morierite, cordierite, zirconia minerals and the like; proteins bound to silica, titania, and the like; silicon-containing polymers; and polyhydroxyalkanoic acid:salt complexes. Such particles, when used in toothpaste, may act as an abrasive material, and thus may supplement, or perhaps even replace, the abrasive materials commonly used in toothpastes.

The more preferred degradable materials are polymers such as polyglycolic acid, polylactic acid, and copolymers of glycolic acid and lactic acid, and esters of glycerol. These polymers are well-known and commercially available. For example, polyglycolic acid is available from the American Cyanamid Company (Dexon®) and Polysciences, Inc.; polylactic acid is available from Polysciences, Inc.; and copolymers of glycolic acid and lactic acid are available from American Cyanamid Company (Vicryl®), Ethicon, Inc. (Polyglactin 910) and Polysciences. Alternatively, the polymers can be synthesized according to known procedures. For example, polyglycolic acid can be prepared employing the ring opening polymerization of the dimeric ester of glycolic acid; polylactic acid can be prepared employing the ring opening polymerization of the dimeric ester of lactic acid; and copolymers of glycolic acid and lactic acid can be prepared employing the ring opening polymerization of the corresponding dimeric esters.

Other preferred degradable polymeric materials are commercially available and/or may be prepared by known procedures.

The particles optionally include a thin, non-porous, water-stable coating that prevents the particle from degrading or swelling when the particle is stored or incorporated into aqueous systems. Preferred coating materials include poly (methyl methacrylate), polystyrene, beeswax, carnauba wax, petroleum wax, polyhydroxyalkanoic acid, glycolipids, glycerides, phospholipids, and glycerol distearate. The coating materials may be materials (like polystyrene, waxes, or poly(methyl methacrylate) that do not degrade when exposed to enzymes in the mouth, or may be materials (like glycerol distearate, polydroxyalkanoic acid, and glycerides) that do degrade when exposed to enzymes in the mouth. All of these materials are commercially available. Preferably the coating constitutes no more than about 10% of the particle diameter.

In alternative embodiments, the particles are composed entirely of the degradable material. The degradable material may be a non-water stable material, or may be a material like glycerol distearate that is water stable but degrades when exposed to mouth enzymes.

The preferred particles can be made by numerous conventional, well-known methods. These include solvent evaporation methods, with or without a surface active agent as necessary, coacervation in all its various forms, pan coating, air-suspension coating, press coating, spray-drying, rotational suspension-separation techniques, melt coating methods, interfacial polymerization, melt-granulation processes and any and all related methods that yield the desired particles as described. Such methods may or may not use organic solvents. Such methods may encapsulate from solution, from the melt or in powdered (solid state) form. Once formed, the particles may be chemically modified (e.g., charged or made magnetic). The particles are then coated with a water stable material. See, for example, the particle-making and particle-coating procedures described generally in Parrott, *Pharmaceutical Technology*, pp. 86–91 (Burgess Pub. Co. 1970); Deasy, *Microencapsulation and Related Drug Procedures*, pp. 1–60 (Marcel Dekker, Inc. 1984); Muller et al., *J. Controlled Release*, 20 (1992) :237–246; Pekarek et al., *Nature*, v. 367 (1994):258–60; Muller et al., *Pharm. Pharmacol. Lett.* v. 3 (1993):67–70; and Juliano (ed.), *Drug Delivery Systems* (Oxford University Press 1980).

To desensitize a hypersensitive tooth, the tooth surface initially is polished. The preferred particles then are applied to the polished surface. Application can take numerous forms. For example, the particles may be applied in the form of an aqueous dispersion that includes, e.g., between 0.01% and 5% particles by weight, that is agitated against the tooth surface for 1–5 minutes. Alternatively, the surface is exposed to a pressurized jet of the aqueous dispersion e.g., at a pressure of about 30 psi for about 20 seconds, or the surface is brushed with bristles that are saturated with particles, for 1–3 minutes. Each of these procedures, when performed on a tooth that had been removed from the mouth, is effective at blocking the exposed tubules in the dentin of the tooth with the particles.

Figure 1B:
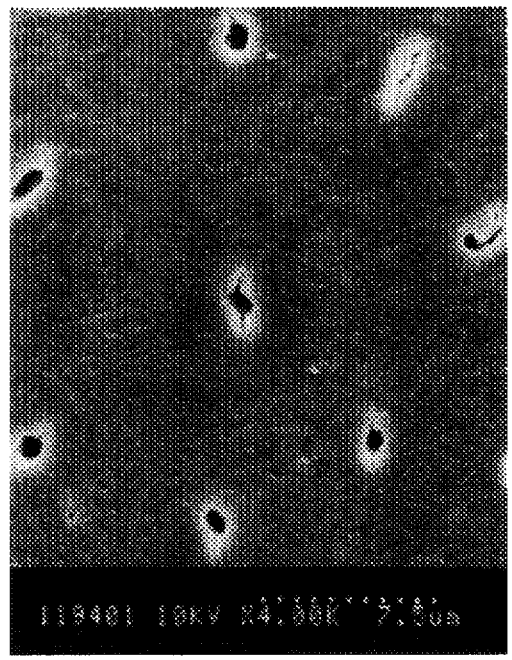
Figure 2A:
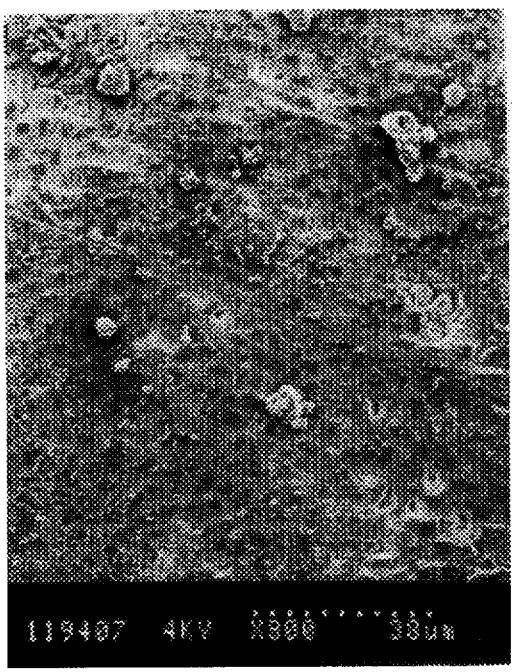
FIGS. 2a and 2b are electron micrographs of a dentin surface after exposure to the particles of the invention.
Figure 2B:
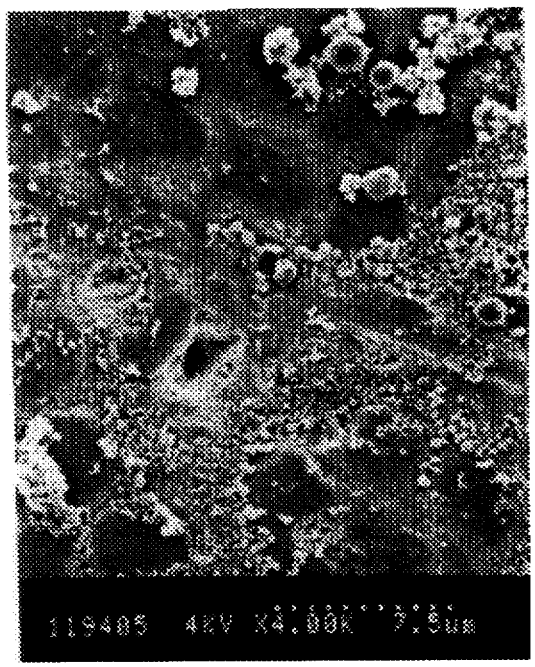

FIGS. 1a, 1b, 2a and 2b show the dentin surface before (1a and 1b) and after (2a and 2b) a 5 minute exposure to a 0.5% (by weight) aqueous dispersion of poly(lactide-co-glycolide) ("PLGA") particles. Prior to exposure to the dispersion, the exposed tubules in the dentin are empty; after exposure they are substantially filled with the particles present in the dispersion. (FIGS. 1a and 2a were both taken at 800× magnifications, and FIGS. 1b and 2b were both taken at 4000× magnifications).

An alternative procedure for applying the particles to the tooth is to soak a cotton pellet with an aqueous dispersion of the particles, and then rub the cotton pellet for 1–3 minutes over the polished surface of the tooth.

The PLGA particles used in the above example were prepared according to the following procedure:

1. 100 mg of PLGA (80:20) were dissolved in 5 mL of methylene chloride.
2. 100 mL of a 0.10% polyvinyl alcohol (PVA) solution in water was prepared. The polyvinyl alcohol was 13,000–23,000 MW and was 87–89% hydrolyzed.
3. The PVA solution was stirred with a Tekmar high speed mechanical stirrer (24,000/min).
4. The PLGA solution was added all at once to the PVA solution. This solution was stirred in a fume hood for 20 min. to drive off the methylene chloride.
5. The resulting suspension was centrifuged. The particles were washed with distilled water. Micrographs showed that a polydisperse particle size distribution resulted (0.1–1 μm) and that the particles were irregular in shape.

Other embodiments are within the claims. For example, the particles can be included in a dentifrice (toothpaste) or a mouthwash; when the dentifrice or mouthwash contacts the surface of a tooth the particles will fill in the tubules. This approach can be used, in particular, to replenish particles that were previously blocking a tubule but have, to some extent, washed out of the tubule or degraded over time. If a mouthwash is used, it may be applied under pressure, using any commercially available water-jet appliance (e.g., a Braun MO 5000). The particles can also be applied, for example, by including them on the bristles of toothbrushes or on dental floss. While the times, pressures and other conditions given above were preferred in a laboratory setting or home use, these conditions may be varied as desired to adapt them to a clinical setting, provided the time, pressure etc., is adequate to block the tubules. Effective conditions may be readily determined by those skilled in the art, e.g. by determining whether a patient's tooth is still sensitive after the treatment.

The filling of dentin tubules with the particles can be enhanced by using particles with a charged outer surface, or by using a swellable material like polyvinyl alcohol in the particles. When the particles include a swellable material, the particles preferably comprise a water-stable exterior. Significantly, a coated particle including a swellable material may be sufficiently small to flow readily into the tubules. But during application part or all of the coating deteriorates allowing water to contact the swellable material. As this material swells the particles become more tightly lodged in the tubule.

In addition, the particles may have an antimicrobial, analgesic or other therapeutic substance adsorbed on their surface or dispersed throughout the interior. These particles provide both the desensitization benefit of this invention, and an anti-microbial benefit or other benefit provided by the therapeutic agent selected. Examples of preferred antimicrobial agents, and how they may be incorporated throughout the particles, are described in U.S. Ser. No. 08/322,926, filed Oct. 13, 1994.

Thus particles having essentially the same composition, e.g., degradable material and anti-microbial agent, can serve two functions, particularly when the particles are sufficiently small to fit readily in normal sized dentin tubules. But the particles may serve only one function (release of anti-microbial agent) if the particles are too large to effectively clog dentin tubules. A composition, e.g., an oral rinse, may include particles that are small enough to serve both functions and particles having the same composition that do not desensitize the tooth. To determine whether such an oral rinse (or other composition) contains particles having an average diameter within applicant's preferred (0.01 micron to 3 micron) or more preferred (0.2 micron to 0.6 micron) ranges, the particle size distribution of all of the essentially identically composed particles in the composition initially is determined. If at least 5% of the particles have an average diameter of between 0.01 micron and 3 micron, or more preferably between 0.2 micron and 0.6 micron, the oral rinse includes particles that have an average particle size within the applicant's preferred or more preferred range.

What is claimed is:

1. A method for desensitizing a hypersensitive tooth in a mouth of a patient, said hypersensitive tooth comprising exposed dentin tubules extending from a paupal surface to the peripheral surface located under the enamel and cementum of said tooth that is exposed in said mouth of said patient and whose exposure is responsible for hypersensitivity, said method comprising contacting said surface of said tooth and said exposed tubules with particles, comprising a degradable material, that are sufficiently small to block or clog said dentin tubules in an amount effective to thereby desensitize said tooth.

2. The method of claim 1, wherein said particles have an average diameter of 0.01 micron to 3 microns.

3. The method of claim 1, wherein said particles have an average diameter of 0.2 micron to 0.6 micron.

4. The method of claim 1, further comprising polishing said surface of said tooth prior to contacting said tooth with said particles.

5. The method of claim 1, wherein said degradable material comprises polyglycolic acid.

6. The method of claim 1, wherein said degradable material comprises polylactic acid.

7. The method of claim 1, wherein said degradable material comprises a copolymer of glycolic acid and lactic acid.

8. The method of claim 1, wherein said degradable material comprises glycerol distearate.

9. The method of claim 1, wherein said degradable material comprises an ester of glycerol.

* * * * *